(12) United States Patent
Teh et al.

(10) Patent No.: US 8,532,949 B2
(45) Date of Patent: Sep. 10, 2013

(54) COMPUTER-IMPLEMENTED METHODS AND SYSTEMS FOR CLASSIFYING DEFECTS ON A SPECIMEN

(75) Inventors: Cho Huak Teh, Cupertino, CA (US); Tommaso Torelli, Berkeley, CA (US); Dominic David, Campbell, CA (US); Chiuman Yeung, Sunnyvale, CA (US); Michael Gordon Scott, Santa Cruz, CA (US); Lalita A. Balasubramanian, Fremont, CA (US); Lisheng Gao, Morgan Hill, CA (US); Tong Huang, San Jose, CA (US); Jianxin Zhang, Santa Clara, CA (US); Michal Kowalski, Santa Cruz, CA (US); Jonathan Oakley, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 1708 days.

(21) Appl. No.: 11/249,144

(22) Filed: Oct. 12, 2005

(65) Prior Publication Data
US 2006/0082763 A1    Apr. 20, 2006

Related U.S. Application Data

(60) Provisional application No. 60/618,475, filed on Oct. 12, 2004.

(51) Int. Cl.
*G01N 37/00* (2006.01)
(52) U.S. Cl.
USPC ........... 702/81; 250/307; 356/237.2; 382/145
(58) Field of Classification Search
USPC ................. 702/35, 81–83; 250/307; 356/72, 356/237.2; 382/145, 149, 224; 703/6, 13
See application file for complete search history.

(56) References Cited

U.S. PATENT DOCUMENTS 6,104,835 A    8/2000  Han
6,757,645 B2 *  6/2004  Chang et al. .................... 703/13
(Continued)

FOREIGN PATENT DOCUMENTS

JP      2002-014054     1/2002
JP      2003-317082    11/2003
WO       01/40145       6/2001

OTHER PUBLICATIONS

International Search Report and Written Opinion for PCT/US2005/036598 mailed Sep. 11, 2006.

(Continued)

*Primary Examiner* — John H Le
(74) *Attorney, Agent, or Firm* — Ann Marie Mewherter

(57) ABSTRACT

Various computer-implemented methods for classifying defects on a specimen are provided. One method includes assigning individual defects detected on the specimen to defect groups based on one or more characteristics of the individual defects. The method also includes displaying information about the defect groups to a user. In addition, the method includes allowing the user to assign a classification to each of the defect groups. Systems configured to classify defects on a specimen are also provided. One system includes program instructions executable on a processor for assigning individual defects detected on the specimen to defect groups based on one or more characteristics of the individual defects. The system also includes a user interface configured for displaying information about the defect groups to a user and allowing the user to assign a classification to each of the defect groups.

24 Claims, 5 Drawing Sheets

(56) References Cited

U.S. PATENT DOCUMENTS

| | | | |
|---|---|---|---|
| 6,968,079 B2* | 11/2005 | Yoshikawa et al. | 382/145 |
| 7,027,143 B1* | 4/2006 | Stokowski et al. | 356/237.2 |
| 2002/0001404 A1 | 1/2002 | Yoshikawa et al. | |
| 2002/0019729 A1 | 2/2002 | Chang et al. | |
| 2003/0202703 A1 | 10/2003 | Ogi | |
| 2004/0028276 A1* | 2/2004 | Okuda et al. | 382/224 |
| 2004/0156540 A1 | 8/2004 | Gao et al. | |
| 2004/0156640 A1 | 8/2004 | Dress et al. | |
| 2004/0218806 A1* | 11/2004 | Miyamoto et al. | 382/145 |
| 2005/0087686 A1* | 4/2005 | Honda et al. | 250/307 |
| 2006/0274932 A1* | 12/2006 | Ikeda et al. | 382/145 |

OTHER PUBLICATIONS

International Preliminary Report on Patentability for PCT/US2005/036598 mailed Apr. 26, 2007.
Office Action for Japanese Patent Application No. 2007-536825 mailed Feb. 8, 2011.
Office Action for Japanese Patent Application No. 2007-536825 mailed Jan. 17, 2012.
Office Action for Korean Patent Application No. 10-2007-7009403 mailed May 14, 2012.
First Office Action for Chinese Patent Application No. 200580034951.X mailed May 9, 2008.
Second Office Action for Chinese Patent Application No. 200580034951.X mailed Oct. 31, 2008.
Notice of Rejection for Chinese Patent Application No. 200580034951.X mailed Apr. 10, 2009.
Notice of Reexamination for Chinese Patent Application No. 200580034951.X mailed Aug. 17, 2010.
Notice of Reexamination for Chinese Patent Application No. 200580034951.X mailed Jun. 14, 2011.
Notice of Final Rejection for Korean Patent Application No. 10-2007-7009403 mailed Dec. 26, 2012.
Dismissal of an Amendment for Japanese Patent Application No. 2007-536825 mailed Feb. 12, 2013.
Final Decision of Rejection for Japanese Patent Application No. 2007-536825 mailed Feb. 12, 2013.
Decision of Refusal of Amendment and Notice of Results of Re-Consideration Prior to Appeal for Korean Application No. 10-2007-7009403 mailed May 29, 2013.

* cited by examiner

COMPUTER-IMPLEMENTED METHODS AND SYSTEMS FOR CLASSIFYING DEFECTS ON A SPECIMEN

PRIORITY CLAIM

This application claims priority to U.S. Provisional Application No. 60/618,475 entitled "Computer-Implemented Methods and Systems for Classifying Defects on a Specimen," filed Oct. 12, 2004, which is incorporated by reference as if fully set forth herein.

BACKGROUND OF THE INVENTION

1. Field of the Invention

The present invention generally relates to computer-implemented methods and systems for classifying defects on a specimen. Certain embodiments relate to a computer-implemented method that includes allowing a user to assign a classification to defect groups to which individual defects detected on a specimen are assigned based on one or more characteristics of the individual defects.

2. Description of the Related Art

The following description and examples are not admitted to be prior art by virtue of their inclusion in this section.

Wafer inspection systems often find thousands of anomalies (commonly called "events" or "defects") on each wafer. Defects may have many forms such as structural flaws, process residues, and external contamination that may occur during semiconductor wafer fabrication. As processes for making wafers evolve, the defect types that are of interest change. The importance of a defect depends on several factors such as appearance and other characteristics such as size and location.

Classifying defects found on wafers and other specimens has, therefore, become increasingly important in order to determine what kinds of defects are present on the wafers in addition to distinguishing the defect types of interest from other defect types. Classifying defects may also include determining if defects are actual defects or nuisance defects. Nuisance defects can be generally defined as a portion of a specimen that appears to be a defect during inspection but is not actually defective.

Generally, classification is performed after wafer inspection has been completed. In addition, classification is usually performed during defect review or after defect review. Defect review generally involves using a different tool than that which was used for inspection. For instance, defect detection is usually performed using an optical inspection tool while defect review is usually performed using an electron beam review tool. However, defect review may be performed using an optical review tool that has a higher magnification or resolution than the optical inspection tool. In this manner, the defect review tool can be used to gain more detailed information about possible defects. As such, the information generated by the defect review tool may be particularly suitable for defect classification.

In the past, defect classification has been performed in several different ways. For example, defect classification can be performed completely manually by an operator. Typically, the operator is presented with defect images or other defect data for each defect sequentially one at a time. The operator then assigns a classification (e.g., pit, particle, etc.) to the defect based on defect appearance and possibly other characteristics (e.g., roughness). Experienced operators can be fairly efficient at classifying defects on wafers. However, manual defect classification performed by even the most skilled and experienced operators takes an unacceptably long time. For instance, the operator typically classifies individual defects one at a time. In this manner, regardless of how skilled the operator is, the time that is needed to perform classification will necessarily depend on how many defects were detected on the wafer. Furthermore, reviewing many defect images or other data repetitively one after another will necessarily produce operator fatigue and loss of concentration. Therefore, even a skilled operator may mistakenly classify defects due to diminished alertness. Furthermore, it can be fairly expensive to employ an operator to review and classify defects particularly since manual defect classification as described above is so time intensive.

Since there are a fair number of disadvantages to currently used methods for manual defect classification, efforts have been made to automate the defect classification process. Several fully automatic defect classification (ADC) tools are now available. Typically, these tools use classification "recipes" to perform defect classification. A "recipe" can be generally defined as a set of instructions that define an operation to be performed by a tool and that are provided to and run on the tool upon request by a user. The recipes are typically generated using previous data about specific defect classes that may be assembled in a suitable database. In the simplest implementation, the ADC tool can then compare unknown defects to those included in the specific defect classes to determine which defect class the unknown defect is most like. Obviously, much more complicated algorithms can be used by the ADC tool to determine which of the defect classes the unknown defect most likely belongs to.

The concept of ADC is fairly simple. However, the implementation has proven to be fairly complex and difficult. For example, generating a suitable database for an ADC recipe usually involves locating a substantial number of each defect type on wafers using wafer inspection and manual defect classification, which may be performed as described above. The data for each defect of a particular type may then be combined into a suitable database. The defect data that is included in the database may be selected by the user. This set of representative defect data may be commonly referred to as a "training set." Although a database generated as described above may be relatively accurate, generating the database is typically time consuming and expensive. In addition, since an ADC recipe tends to be accurate for only those defects that are fairly similar to those in the training set, ADC recipes may be useful only for substantially similar processes which tend to produce the same kinds of defects over time. Defects that are not sufficiently similar to those in the database may be incorrectly classified or not classified at all. Accordingly, ADC recipes usually cannot be used for different processes or different types of specimens, and therefore, many such recipes may be generated depending on the defects and specimens to be inspected. As such, the inflexibility of ADC recipes may increase the cost of ADC since each time a process or device is changed, the ADC recipe may need to be updated manually. In addition, the time and expense of generating many different ADC recipes may be substantially prohibitive.

Despite the drawbacks of the various types of defect classification methods and tools described above, defect classification will only increase in importance in semiconductor device manufacturing in the future. For example, defect classification can be used to identify problems with semiconductor fabrication processes. In addition, defect classification can be used to identify problems with semiconductor device designs. Therefore, since the results of defect classification may be used to make yield management decisions about semiconductor processes and designs, the accuracy of the defect classification may have a direct effect on the success of semiconductor manufacturing.

Accordingly, it may be advantageous to develop computer-implemented methods and systems for classifying defects on a specimen that are relatively inexpensive, quick, accurate, flexible, and easily account for unexpected defect types on many different types of wafers or other specimens.

SUMMARY OF THE INVENTION

The following description of various embodiments of methods and systems is not to be construed in any way as limiting the subject matter of the appended claims.

An embodiment of the invention relates to a computer-implemented method for classifying defects on a specimen. The method includes assigning individual defects detected on the specimen to defect groups based on one or more characteristics of the individual defects. In one embodiment, the one or more characteristics include defect feature vectors, extracted features, feature attributes, or some combination thereof. In some embodiments, the one or more characteristics are determined from data generated by electron beam review of the individual defects. In other embodiments, the one or more characteristics are determined from data generated by electron beam review of the individual defects in combination with data generated by optical inspection of the specimen.

In an embodiment, the method includes selecting a classification recipe based on one or more characteristics of the specimen. For example, the classification recipe may be selected based on the devices being formed on the specimen. In a different embodiment, the method includes selecting a classification recipe based on one or more processes performed on the specimen. In both embodiments, assigning the individual defects to defect groups may include using the classification recipe to assign the individual defects to the defect groups. In other embodiments, assigning the individual defects to defect groups includes using automatic defect classification codes to assign the individual defects to the defect groups. In an alternative embodiment, assigning the individual defects to defect groups includes using natural grouping to assign the individual defects to the defect groups.

In one embodiment, the defect groups include a defect group for the individual defects that have one or more unrecognized characteristics. In another embodiment, the defect groups include a defect group for the individual defects that were detected by inspection but were not re-detected by review.

The method also includes displaying information about the defect groups to a user. In some embodiments, the information that is displayed to the user includes probable classifications for the defect groups. In another embodiment, the information includes information about one or more typical defects (e.g., non-outliers) included in each of the defect groups. In an additional embodiment, the information includes data about one or more of the individual defects. The data may be generated by an electron beam review tool. Alternatively, or additionally, the data may be generated by an optical inspection tool.

In addition, the method includes allowing the user to assign a classification to each of the defect groups. The method may also include allowing the user to move one or more of the individual defects from one of the defect groups to another of the defect groups. In some embodiments, the method includes allowing the user to create one or more additional defect groups and to move one or more of the individual defects from the defect groups into the one or more additional defect groups.

In further embodiments, the method includes generating a classification recipe based on the classifications assigned by the user. In this manner, the method may include generating a classification recipe "from scratch." The classification recipe can be used in semi-automatic defect classification methods and automatic defect classification methods. In another embodiment, assigning the individual defects to defect groups includes using a classification recipe to assign the individual defects to the defect groups. The classification recipe may be selected as described above. Such an embodiment of the method may also include altering the classification recipe based on the classifications assigned by the user. In this manner, the method may include "correcting" or "updating" an existing classification recipe. In an additional embodiment, the method includes generating a training set based on the classifications assigned by the user.

The method may also include analyzing the individual defects, the specimen, processes performed on the specimen, or a combination thereof based on the classifications assigned by the user. In addition, the method may include making yield management decisions based on the classifications assigned by the user. Each of the embodiments of the method described above may include any other step(s) described herein.

Another embodiment relates to a different computer-implemented method for classifying defects on a specimen. This embodiment includes assigning individual defects detected on the specimen to defect groups based on one or more characteristics of the individual defects. The individual defects may be assigned to defect groups as described above. The method also includes displaying information about the defect groups to a user. The information includes a classification assigned to each of the defect groups. In addition, the method includes allowing the user to confirm or alter the classification assigned to each of the defect groups. This method may also include any other step(s) described herein.

An additional embodiment relates to a system configured to classify defects on a specimen. The system includes program instructions executable on a processor for assigning individual defects detected on the specimen to defect groups based on one or more characteristics of the individual defects. The system also includes a user interface configured for displaying information about the defect groups to a user and allowing the user to assign a classification to each of the defect groups.

In one embodiment, allowing the user to assign a classification to the defect groups includes allowing the user to confirm or reject a classification that is assigned to each of the defect groups by the program instructions. In another embodiment, allowing the user to assign a classification to the defect groups includes allowing the user to alter a classification that is assigned to each of the defect groups by the program instructions. Each of the embodiments of the system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
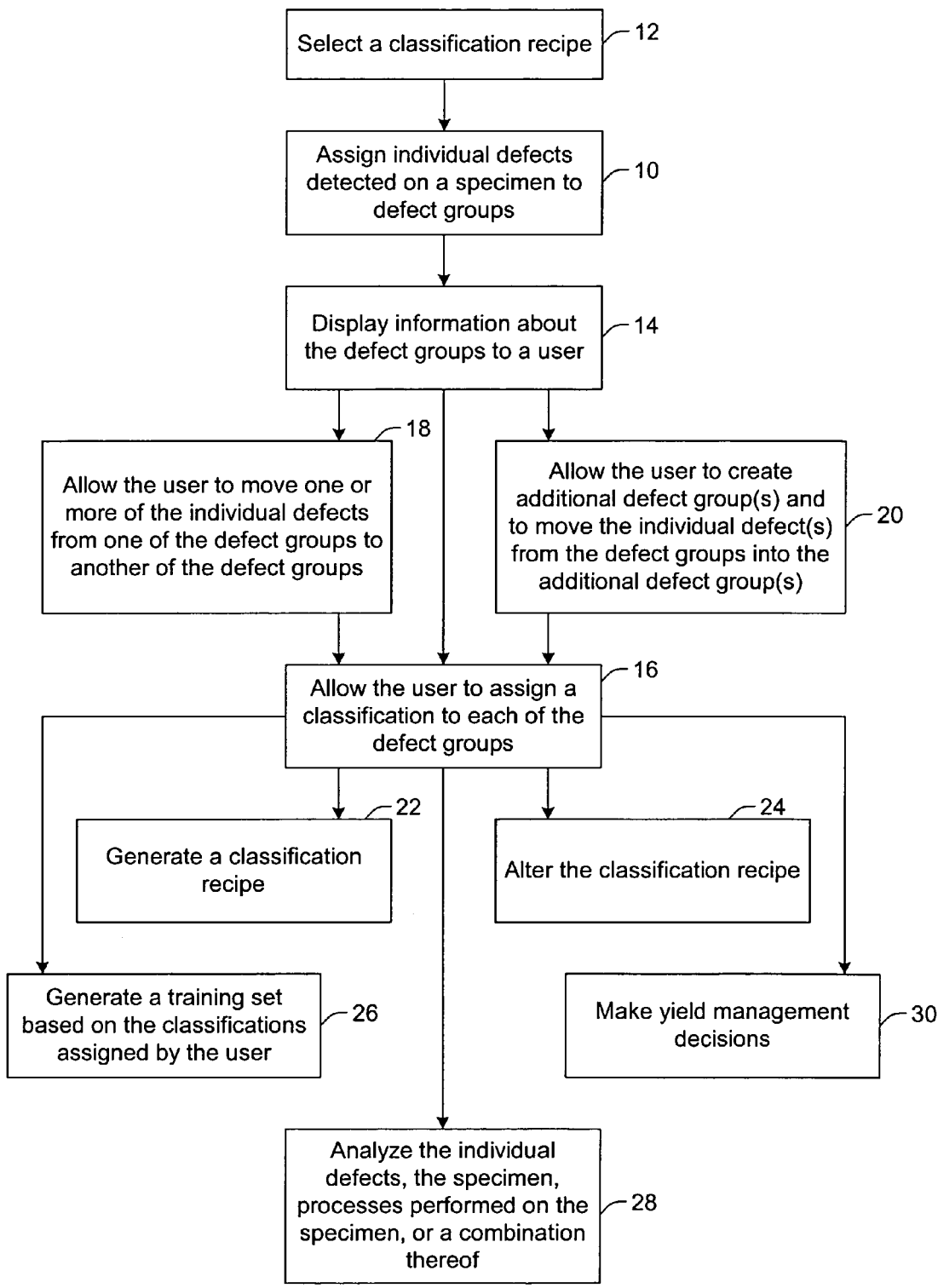
FIG. 1 is a flow chart illustrating one embodiment of a computer-implemented method for classifying defects on a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "defects" refers to any anomalies that may be found on a specimen. As used herein, the term "specimen" refers to a wafer or any other specimen known in the art such as a reticle, which may also be commonly referred to as a "mask." Although embodiments are described herein with respect to a wafer, it is to be understood that the embodiments may be used to classify defects detected on any other specimen known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers formed upon a substrate. For example, such layers may include, but are not limited to, a resist, a dielectric material, and a conductive material. A resist may include any material that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer.

The methods described herein may be generally described as semi-automatic defect classification methods. The methods described herein may also be described as power assisted classification (PAC) methods. For example, the methods described herein generally include automatic grouping of defects based on one of more characteristics of the defects. The groups of defects may then be classified by a user. In one such example, the user may be presented with a probable, or possible, classification for a group of defects along with some information about the defects. The user may then confirm or reject the proposed classifications. In addition, the user may alter the proposed classifications. In this manner, the methods include both automatic and manual steps.

The methods and systems described herein provide advantages over other defect classification methods and systems such as those described above (e.g., manual classification or automatic classification). For example, the methods described herein provide significant user control over the classifications that are ultimately assigned to defect groups. However, the user can classify defects without having to classify individual defects one at a time as in manual classification methods that are currently available. As such, the methods described herein are much quicker, efficient, and less expensive than manual classification methods. In addition, since the methods and systems described herein provide the user with the ability to correct the grouping of individual defects and the classifications assigned to defect groups, the methods and systems described herein may be more accurate than automatic defect classification (ADC) methods while providing many of the advantages of ADC (e.g., high throughput).

Furthermore, the methods and systems described herein may be used to dynamically create and update classification recipes based on the results of the methods. In this manner, the methods and systems may be used to create classification recipes that may be used for semi-automatic and/or ADC, which may be more accurate than classification recipes created in other ways. Furthermore, the methods and systems described herein are more flexible than ADC methods in that the characteristic(s) of the defects that are used for grouping may be selected based on information about the specimen, the defects of interest, and/or processes performed on the specimen. Moreover, the methods and systems described herein can be used with a variety of defect data such as data generated by an optical inspection and/or review tool, an electron beam review tool, or a combination of data from both an optical inspection and/or review tool and an electron beam review tool. Additional advantages and further details of the methods and systems for classifying defects can be found in the description provided herein.

Turning now to the drawings, FIG. 1 illustrates one embodiment of a computer-implemented method for classifying defects on a specimen. It is noted that the steps shown in FIG. 1 are not essential to practice of the method. One or more steps may be omitted and/or added to the method illustrated in FIG. 1, and the method can still be practiced within the scope of this embodiment.

The method may begin when a user selects a set of results to classify (not shown). The set of results may be selected using a user interface as described further herein. The method includes assigning individual defects detected on a specimen to defect groups, as shown in step 10. The individual defects are assigned to defect groups based on one or more characteristics of the individual defects. In one embodiment, the one or more characteristics of the defects that are used to group the defects include defect feature vectors, extracted features, feature attributes, or some combination thereof. The defect feature vectors, extracted features, and feature attributes may include any of those known in the art. In addition, the defect feature vectors, extracted features, and feature attributes may be determined in any manner known in the art. One or more of the extracted features may also be weighted, and the extracted features may be compared accordingly as illustrated in PCT Publication No. WO 01/40145 to Baker et al., which is incorporated by reference as if fully set forth herein. Furthermore, the extracted features of defects may be compared to features of classified defects in a database such as a knowledge database as illustrated in U.S. Pat. No. 6,104,835 to Han, which is incorporated by reference as if fully set forth herein.

The one or more characteristics of the defects may be determined from data generated by electron beam review of the individual defects. Electron beam review of the individual defects may be performed with an electron beam review tool such as the eV300 scanning electron microscope (SEM) review tool, which is commercially available from KLA-Tencor, San Jose, Calif., or any other suitable electron beam review tool known in the art. In a different embodiment, the one or more characteristics of the defects may be determined from data generated by optical review of the individual defects. Optical review may be performed using an optical high resolution imaging system such as the 2360 and AIT XP systems, which are both commercially available from KLA-Tencor, or any other optical review tool known in the art. In yet another embodiment, the one or more characteristics of the defects may be determined from data generated by electron beam review of the individual defects in combination with data generated by optical inspection of the specimen. Optical inspection may be performed using the optical systems described above as well as any other optical inspection system known in the art.

The defects may be grouped using any method known in the art. However, unlike other methods and systems, the methods and systems described herein may vary in the way that defects are grouped based on the data that is available. In other words, the behavior of the computer-implemented method may change based on the tools that are available for working with the data. For example, if there is no existing classification recipe for the specimen that was inspected, then the method will work from the data available from inspection and review of the current specimen. The groups of defects into which individual defects are assigned may be determined from input from the user (e.g., the number or types of defects that the user indicates are of interest). In contrast, if there is an existing classification recipe for the layer that has been formed on the specimen prior to inspection, then the method will use that classification recipe as a starting point in setting parameters for the grouping of defects. In addition, if there is an existing classification recipe for the device formed at the layer on the specimen being inspected, the method will use that classification recipe for the grouping of the defects.

In this manner, as shown in step 12, the method may include selecting a classification recipe that will be used to assign the individual defects to the defect groups. The classification recipe may be selected based on one or more characteristics of the specimen and/or one or more processes performed on the specimen. In addition, selection of the classification recipe may be automated by assigning names to the classification recipes that are the same as the names that are assigned to the device level being inspected. In other embodiments, assigning the individual defects to defect groups may include using ADC codes to assign the individual defects to the defect groups. In a different embodiment, assigning the individual defects to defect groups may include using natural grouping to assign the individual defects to the defect groups.

The method also includes displaying information about the defect groups to a user, as shown in step 14. The information may be displayed with a user interface such as those described further herein. Preferably, the information about the defect groups is displayed in a manner such that the user can easily review and evaluate the results of the assignation of individual defects to defect groups and such that the user can perform one or more functions on the individual defects and the defect groups.

For instance, the information may include probable, or possible, classifications for the defect groups. In addition, the information may include probable classifications for less than all of the defect groups. For example, the defect groups may include a defect group for the individual defects that have one or more unrecognized characteristics. In other words, one of the defect groups may include individual defects that could not be assigned to one of the possible defect groups. This defect group may be indicated as "unknown" or with some other suitable defect group identifier that indicates that these defects were not recognized. In addition, the defect groups may include a defect group for individual defects that were detected by inspection but were not re-detected by review. Such defects may or may not be actual defects. Therefore, these individual defects may be grouped together and identified for user review.

The information that is displayed to the user may also include information about one or more typical defects included in each of the defect groups. The typical defect(s) may include non-outlier defects. In this manner, the typical defects may include individual defects that are generally representative of the entire defect group. In addition, displaying more than one typical defect to the user may provide the user with an estimate of the average characteristics of the defects in a defect group thereby possibly enabling the user to make a more accurate assessment of the defect group classification.

In addition, data about one or more of the individual defects in one or more of the defect groups that is displayed to a user may include data that is generated by an electron beam review tool. In this manner, the data that is displayed may include SEM images (e.g., top down SEM images and/or cross-sectional SEM images). Preferably, the information that is displayed to the user will be high magnification images since this type of data will visually provide a substantial amount of information about defects to the user. Additionally, or alternatively, the data that is displayed to the user may include data that is generated by an optical inspection tool. For example, optical inspection data may be displayed instead of or in addition to the electron beam review data for individual defects that were not re-detected by review. In this manner, when determining if a detected defect actually exists, the user may review both the data that indicated that a defect was present (e.g., inspection data) in addition to the data that indicated that a defect was not present (e.g., review data).

The method further includes allowing the user to assign a classification to each of the defect groups, as shown in step 16. Assigning a classification to each of the defect groups may include confirming or rejecting classifications that were proposed by the computer-implemented method. In addition, assigning a classification to each of the defect groups may include altering one or more classifications that were proposed by the computer-implemented method. In this manner, the methods and systems described herein provide ultimate control over the assigned classifications to the user. Therefore, the user may correct any classifications that were proposed in error by the computer-implemented method.

The method may also include allowing the user to move one or more of the individual defects from one of the defect groups to another of the defect groups, as shown in step 18. In this manner, the user may correct any incorrect assignments of the individual defects to the defect groups made by the computer-implemented method. In addition, the method may include allowing the user to create one or more additional defect groups and to move one or more of the individual defects from the defect groups into the one or more additional defect groups, as shown in step 20. The ability to create new defect groups may be particularly useful if, for example, unexpected defect types are detected on the specimen. The user may also create new defect groups for subgroups of a particular defect group.

In some embodiments, the method may also include generating a classification recipe, as shown in step 22. The classification recipe may be generated based on the classifications assigned by the user. Such a classification recipe may be used in semi-automatic defect classification methods such as those described herein. In addition, the classification recipe may be used in ADC methods. In this manner, the classification results may be used to create and improve the automatic classification or binning of defects.

In another embodiment, if a classification recipe is used to assign the individual defects to the defect groups, the method may include altering the classification recipe, as shown in step 24. The classification recipe may be altered based on the classifications assigned by the user. In this manner, the results of the classification can be used to improve the classification recipe used for the initial grouping, which can then be used for subsequent defect classification on other wafers. In one mode, a privileged user may be allowed to guide the improvement of the classification recipe. In another style of operation, the classification recipe may be altered automatically. In this manner, the method may be used to generate and update existing classification recipes based on actual defect data, actual classification results, and feedback from a user thereby producing classification recipes that will be "smarter" than classification recipes that are generated in other manners.

Figure 2:
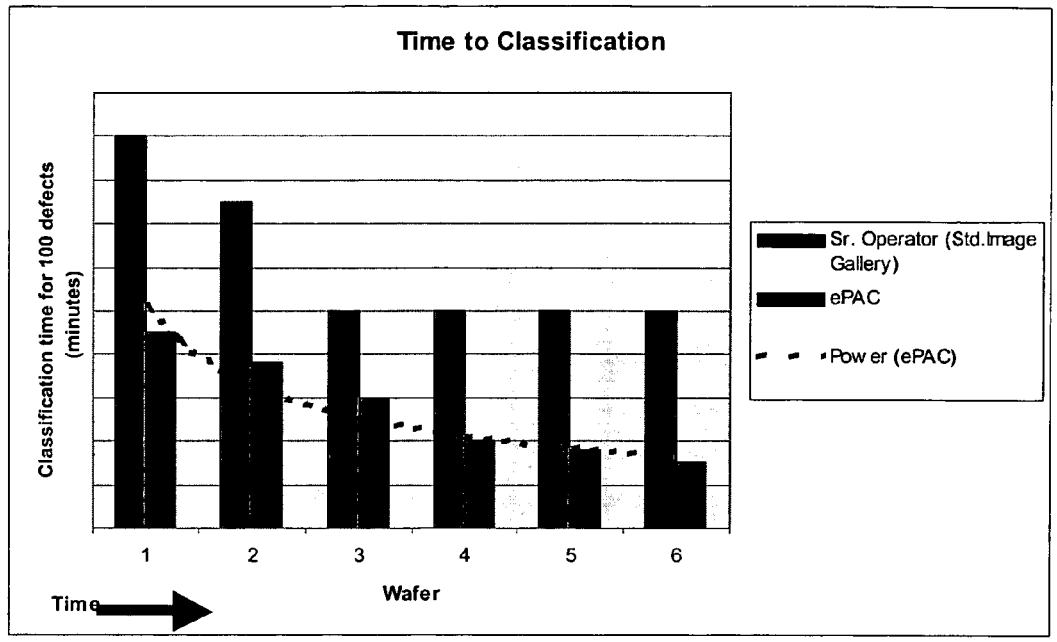
FIG. 2 is a plot illustrating example times to classification that can be expected for embodiments of the methods described herein versus manual classification.

For example, FIG. 2 illustrates the estimated time in which manual classification was completed and the estimated time in which classification was completed using the method described herein for a number of wafers. The times shown in FIG. 2 illustrate the time in which 100 defects on each wafer were classified, which serves to normalize the times across the wafers. The wafers on which defects were classified were similarly processed prior to inspection and review. The manual classification was performed as described above by a senior operator using a standard defect image gallery. The wafers were processed sequentially (i.e., defects were classified on wafer 1, then defects were classified on wafer 2, etc.).

As shown in FIG. 2, for the first three wafers, both the time in which manual classification was completed and the time in which the classification method described herein (which is referred to in FIG. 2 as "ePAC" or "e-beam power assisted classification") was completed decreases. This decrease in the time in which the operator completed manual classification is due at least in part to the operator becoming increasingly familiar with the defects on the wafers as the operator classifies more and more defects. The decrease in the time in which the classification method described herein was completed also is due at least in part to the method becoming increasingly familiar with the defects on the wafers as more defects are classified. In other words, the computer-implemented method becomes "smarter" and quicker by the wafer. This increased familiarity of the computer-implemented method is due at least in part to updating of the classification recipe as defects are classified.

As further shown in FIG. 2, the time in which the operator completed classification of defects on wafers 3-6 was substantially constant. This constant time reflects the fact that although an operator's experience level and familiarity with defects increases over time, at some point, a minimum time to completion will be reached. This minimum time to completion will vary depending on the number of defects that are classified since the operator must classify each defect one at a time. In contrast, the time in which the computer-implemented method completed classification of defects on wafers 3-6 continues to decrease. As shown in FIG. 2, the time in which the computer-implemented method completed classification of defects on wafers 1-6 decreased exponentially. Such a substantial decrease in the defect classification time reflects the fact that the computer-implemented method gets "smarter" as described above for each wafer on which defects are classified. In addition, as shown in FIG. 2, even when the minimum time for classification has been reached for an operator, the computer-implemented method continues to get quicker. In this manner, the throughput of the computer-implemented methods described herein may be substantially higher than the throughput of manual classification.

Figure 3:
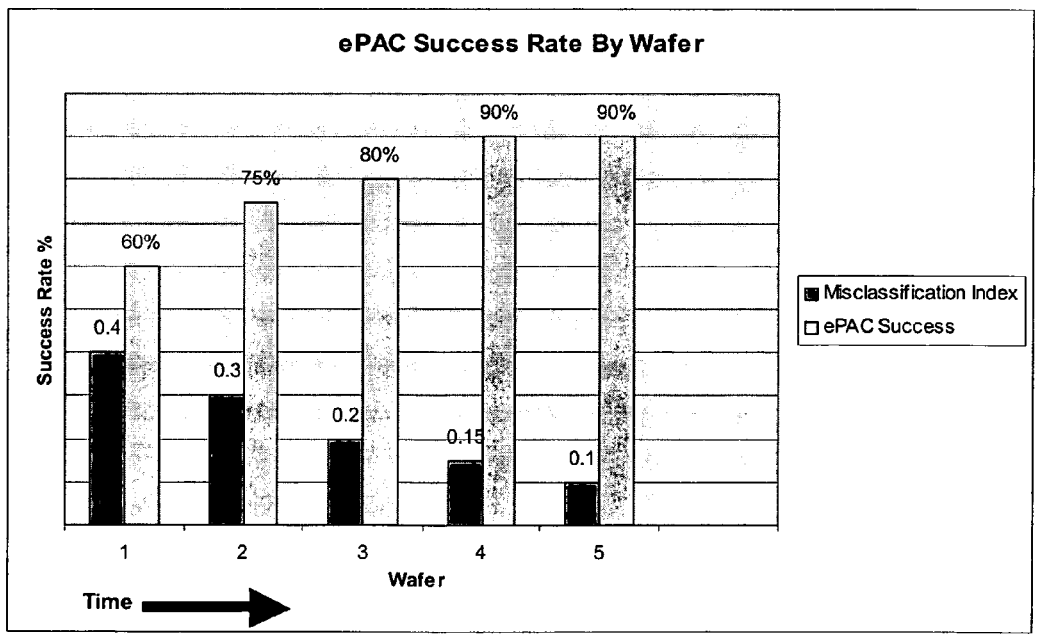
FIG. 3 is a plot illustrating example success rates that can be expected for the embodiments of the methods described herein.

As shown in FIG. 3, the computer-implemented method described herein also becomes more accurate as the number of wafers on which defects are classified increases. For example, as shown in FIG. 3, the success rate or the percentage of defects that were classified correctly by the computer-implemented method increased substantially from 60% to 90% over just 4 wafers. In addition, the misclassification index of the computer-implemented method decreased with each wafer on which defects were classified. In this manner, not only do the computer-implemented methods described herein become quicker over time, they also become more accurate over time. As such, the computer-implemented methods may become particularly suitable for use in ADC methods and tools after they have classified defects on a fair number of wafers.

The method may also include generating a training set based on the classifications assigned by the user, as shown in step 26 of FIG. 1. A training set can be generally defined as a set of data about defects that can be used to define parameters in a classification recipe and can be used to verify defect classifications. The training set, in the methods described herein, can be generated automatically after the user has provided feedback on the defect groups. In addition, the training set may include defect data for more than one specimen. The specimens for which data is included in the training set may include specimens inspected after the same process has been performed on the specimens. In addition, the method may include generating a completely new training set or updating an existing training set. In this manner, the computer-implemented method maintains "memory" of knowledge gleaned from defect classification thereby enabling continuous building of knowledge. Furthermore, the training set may include many more defects of the same type thereby increasing the accuracy of the parameters that define the defect groups.

In some embodiments, the method may include analyzing the individual defects, the specimen, processes performed on the specimen, or a combination thereof, as shown in step 28. Analyzing the individual defects may include, for example, dispositioning the individual defects (e.g., determining if the individual defects can be or should be repaired). Analyzing the specimen may include dispositioning the specimen (e.g., determining if the specimen can be cleaned or otherwise repaired, determining if the specimen should be reworked, determining one or more parameters of one or more processes that will be performed on the specimen, etc.). Analyzing the processes that were performed on the specimen may include, for example, determining if the process tools used for the processes should be maintained, determining if the process is out of spec and if so which parameters of the process should be modified to bring the process back into spec, determining correction terms for one or more parameters of the process, etc. In this manner, since the methods described herein generate valuable information about the types of defects present on a specimen, the methods may include using this information to make informed decisions regarding the defects, the specimens, and/or the processes.

In a similar manner, the method may include making yield management decisions, as shown in step 30. The yield management decisions may be based on the classifications assigned by the user. The yield management decisions may include deciding if and how a process that was performed on the specimen should be altered. Preferably, the process will be altered to reduce the number of defects present on other specimens on which the process is performed. The yield management decisions may also include deciding if and how a process that will be performed on the specimen should be altered. For example, the process that will be performed on the specimen may be altered to compensate for defects and other characteristics of the specimen. In addition, the yield management decisions may include deciding if and how a design of a device that is being formed on the specimen should be altered. For example, if defects are classified by the method as corner rounding of features formed on a level of the specimen, then the method may indicate that optical proximity correction (OPC) features should be added to the design. If OPC features are already included in the design, the method may indicate that the OPC features in the design should be altered. Obviously, this is one example of how a design such as an integrated circuit design may be altered, and the design may be altered in any of a number of other ways.

The embodiments of the method described above, therefore, provide faster, easier, and more reliable semi-manual classification of defects on semiconductor wafers by grouping them in preparation for the classification process. This grouping makes use of the defects' current features and/or attributes as well as using features and/or attributes from other tools that inspected the wafers. The computer-implemented method also "power assists" the user through the classification process. In addition, the classification method described herein can be used as a user-friendly stepping stone to automated classification (for high resolution tools) and binning for inspectors, by sharing information. The manual classifications and the defect images or other defect data may be sent out at the completion of the computer-implemented method (e.g., in the form of a KLARF or other standard file) for use in data analysis.

Figure 4:
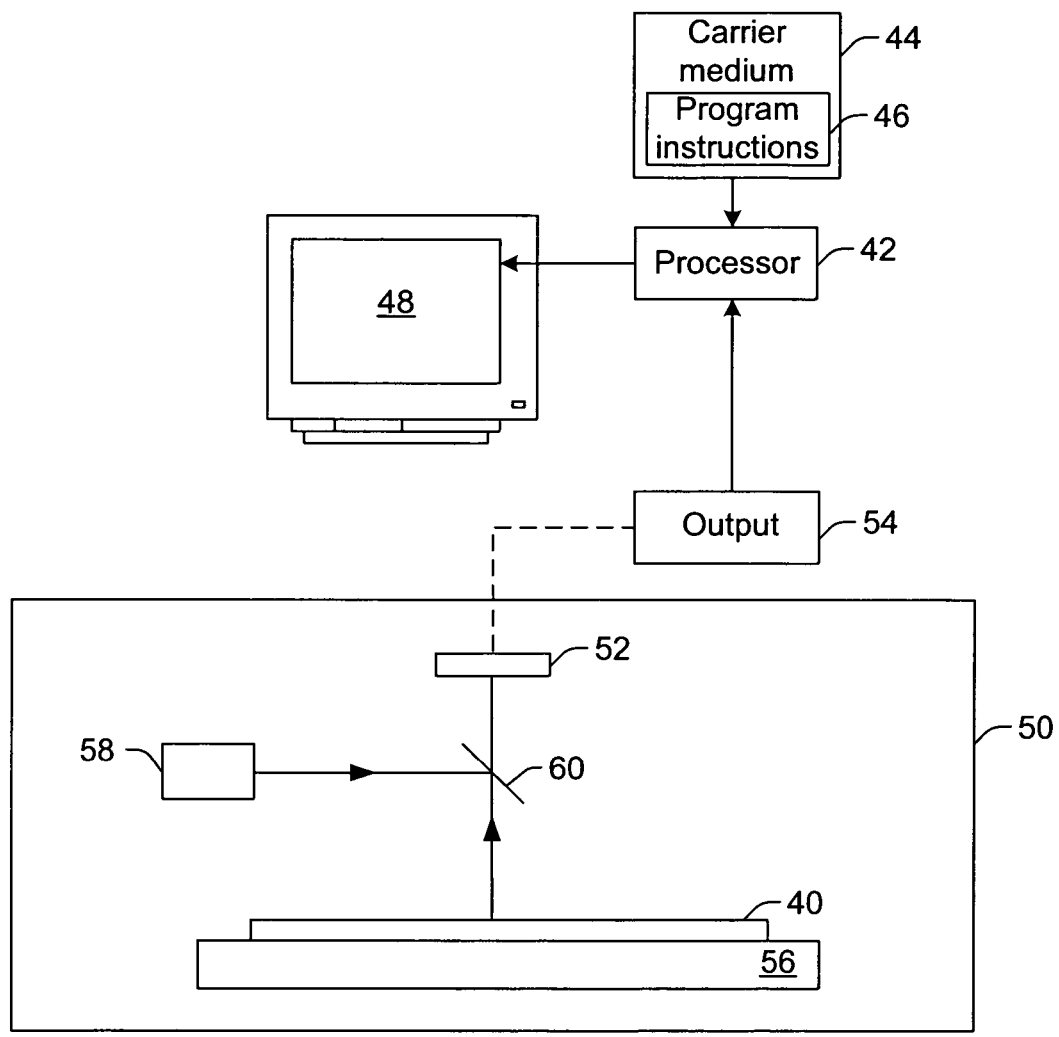
FIG. 4 is a schematic diagram illustrating a side view of one embodiment of a system configured to classify defects on a specimen.

FIG. 4 illustrates one embodiment of a system configured to classify defects on specimen 40. In particular, the system embodiment illustrated in FIG. 4 may be particularly suitable for performing one or more of the computer-implemented methods described herein. The system shown in FIG. 4 is configured to review defects on specimen 40, which may be a wafer. However, the system may have any configuration known in the art that is suitable for review of defects on any other specimen (e.g., a reticle).

The system includes processor 42 and carrier medium 44. Carrier medium 44 includes program instructions 46, which are executable on processor 42. The program instructions are executable on the processor for assigning individual defects detected on the specimen to defect groups based on one or more characteristics of the individual defects. Assigning the individual defects to defect groups may be performed as described above. The program instructions may also be executable for performing any of the additional steps of any of the embodiments of the methods described above. The program instructions may be further configured as described above.

Program instructions implementing methods such as those described herein may be transmitted over or stored on the carrier medium. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The processor may take various forms, including a personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium.

The system also includes user interface 48, which is configured for displaying information about the defect groups to a user and allowing the user to assign a classification to each of the defect groups. The information that is displayed to the user may include any of the information as described herein. Allowing the user to assign classifications may include, in one embodiment, allowing the user to confirm or reject a classification that is assigned to each of the defect groups by the program instructions. In another embodiment, allowing the user to assign classifications may include allowing the user to alter a classification that is assigned to each of the defect groups by the program instructions. The user interface may be configured to perform additional steps as described herein (e.g., allowing the user to move a defect from one defect group to another). Example screenshots of a suitable user interface are described further below. The user interface may be implemented in any manner that is suitable for performing the functions described herein.

The system may be configured as a standalone workstation. In other words, the system may include processor 42, carrier medium 44, program instructions 46, user interface 48, and any other computer-related components (e.g., networking hardware, etc.) but not any inspection or defect review related hardware (e.g., an optical subsystem). Alternatively, the system may include inspection and/or review tool 50. Tool 50 may be configured to review defects on specimen 40 and to generate review data for the specimen that contains information about the defects on the specimen. In some embodiments, tool 50 may be configured to inspect specimen 40 and to generate inspection data for the specimen.

Tool 50 may be coupled to processor 42. For example, one or more components of tool 50 may be coupled to processor 42 by a transmission medium (not shown). The transmission medium may include "wired" and "wireless" portions. In another example, detector 52 of tool 50 may be configured to generate output 54. The output may be transmitted across a transmission medium from detector 52 to processor 42. In some embodiments, the output may also be transmitted through one or more electronic components coupled between the detector and the processor. Therefore, output 54 is transmitted from the tool to the processor, and program instructions 46 may be executable on the processor to classify defects on the specimen using the review data included in output 54.

Inspection and/or review tool 50 may be configured to perform defect review using any technique known in the art. For example, the tool may be configured to form high resolution images of the specimen. In addition, the tool includes stage 56 upon which specimen 40 may be disposed during defect review. The stage may include any suitable mechanical or robotic assembly known in the art. The tool also includes light source 58. Light source 58 may include any appropriate light source known in the art. In addition, the tool may include beam splitter 60, which is configured to direct light from light source 58 onto specimen 40 at angles that are approximately normal to an upper surface of specimen 40. The beam splitter may include any suitable beam splitter known in the art. The tool further includes detector 52, which is configured to detect light transmitted by beam splitter 60. The detector is also configured to generate output 52. The detector may include any suitable detector known in the art.

Although one general configuration of an inspection and/or review tool is shown in FIG. 4, it is to be understood that the tool may have any suitable configuration known in the art. For example, inspection and/or review tool 50 may be replaced with the measurement head of the 2360 tool, one of the AIT family of tools, or non-optical defect review tools such as the eV300 SEM review tool, all of which are commercially available from KLA-Tencor. In addition, the inspection and/or review tool may include other optical systems such as ellipsometer-based systems, scatterometer-based systems, etc. and/or e-beam systems such as a CD SEM and the eS25 and eS30 systems, which are commercially available from KLA-Tencor.

Figure 5:
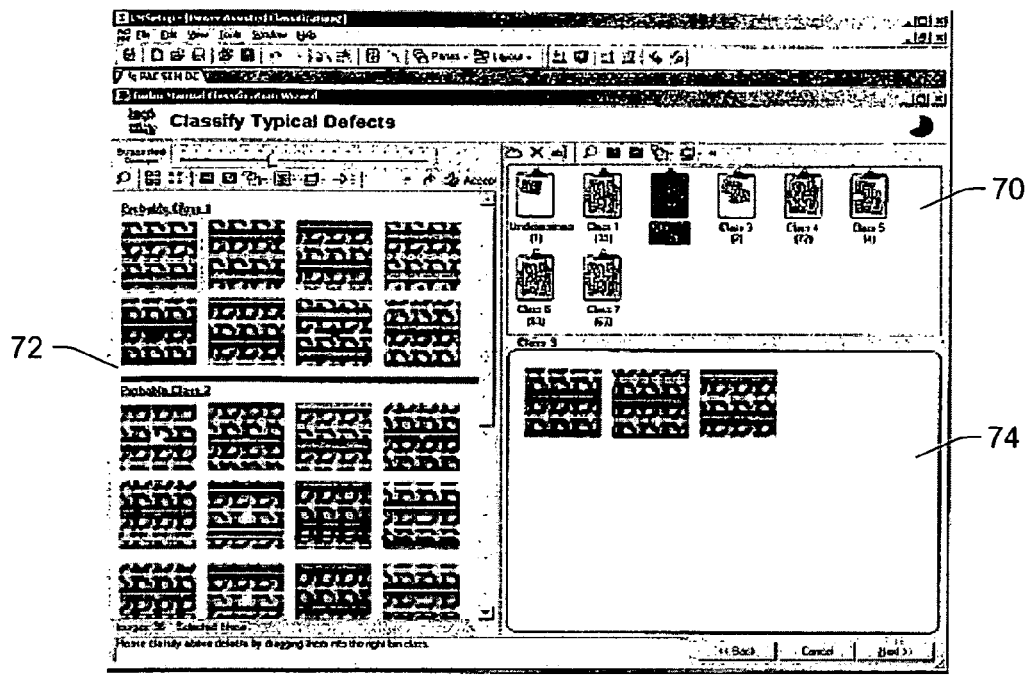
FIGS. 5-7 are screenshots illustrating examples of a user interface that can be included in the embodiments of the systems described herein.

FIG. 5 is a screenshot that illustrates one example of a user interface that can be used to perform one or more of the functions described above. Top, right hand side 70 of the user interface displays the defect groups into which individual defects were assigned and the number of defects that were assigned to each group. In this example, the number of defect groups into which defects were assigned is based on the number of groups that were selected by the user. Such defect groups may be suitable particularly when a classification recipe is not available for use by the computer-implemented method.

Left hand side 72 of the user interface displays the grouping of defects by illustrating only a sample of the typical defects. In other words, typical representatives of the feature space are shown in this screenshot, and outlier defects are not displayed in this example. In the screenshot of FIG. 5, the typical defects of probable class 1 and probable class 2 are illustrated in the left hand side of the user interface, and typical defects in other probable classes can be displayed by using the scroll bar to the right of left hand side 72 of the user interface. Although the individual defects are displayed in this example using defect images, it is to be understood that the individual defects may be displayed to the user with any other defect data known in the art, and particularly any other defect data that is meaningful to a user. In addition, although only one type of defect images are shown in the user interface of FIG. 5, it is to be understood that the user interface may display more than one type of defect data to the user.

As shown in FIG. 5, the user can select defects assigned to defect groups (e.g., classes 1 and 2) illustrated on the left hand side of the user interface and can move the selected defects into other defect groups (e.g., class 3) on bottom, right hand side 74 of the user interface. Such moving of defects can be easily accomplished by clicking and dragging individual defect images. In a similar manner, the user may create one or more additional defect groups on the right hand side of the user interface. In addition, the user may assign individual defects to the additional defect group(s) as described above. In this manner, the user can work in a customized gallery to move defects from the groupings into classification "bins." Furthermore, additional defects may be moved and/or binned in the user interface by the system, without user effort, throughout the classification process. After the user has manually edited the individual defects that are included in any defect group, the user may select an option such as "Accept All" displayed in the user interface to accept the individual defects in the defect group. In this manner, the user may confirm that the defect classifications are correct. The user interface may be further configured as shown in FIG. 5. In addition, the user interface may be further configured as described herein.

Figure 6:
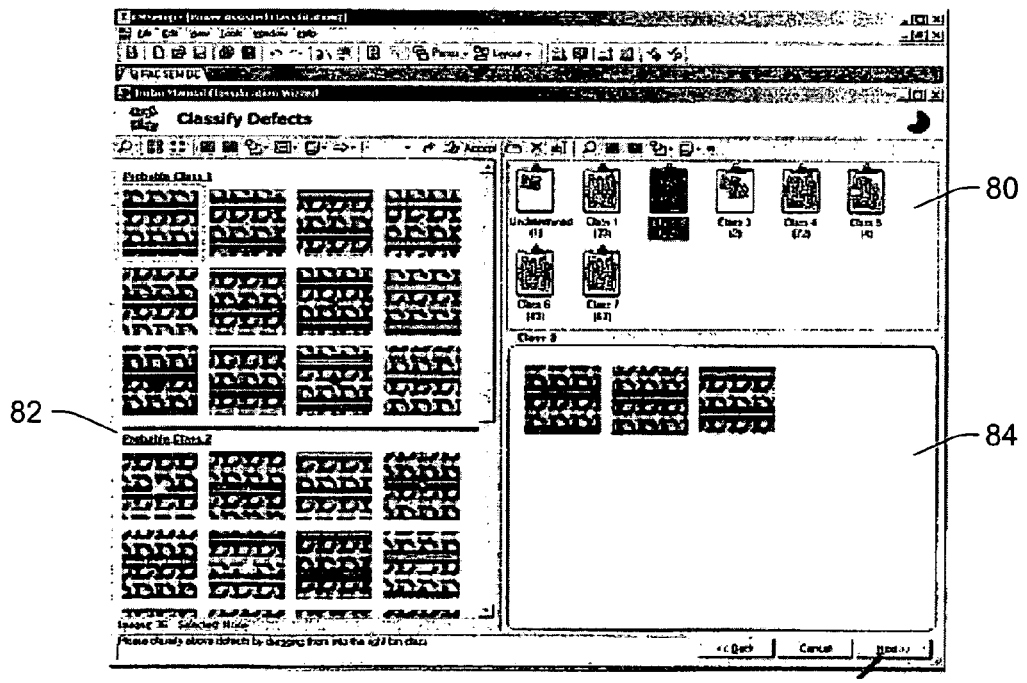

FIG. 6 is another screenshot that illustrates a different example of a user interface that can be used to perform one or more of the functions described above. Top, right hand side 80 of the user interface displays the defect groups into which individual defects were assigned and the number of defects that were assigned to each group. Like the example described above, the number of defect groups into which defects were assigned is based on the number of groups that were selected by the user. Such defect groups may be suitable particularly when a classification recipe is not available for use by the computer-implemented method.

Left hand side 82 of the user interface displays the grouping of defects by illustrating all of the individual defects that were assigned to each of the defect groups. In other words, typical representatives of the feature space as well as outlier defects are displayed in this example. In the screenshot of FIG. 6, the defects of probable class 1 and probable class 2 are illustrated in the left hand side of the user interface, and defects in other probable classes can be displayed by using the scroll bar to the right of the left hand side of the user interface.

As shown in FIG. 6, the user can select defects assigned to defect groups (e.g., classes 1 and 2) illustrated on the left hand side of the user interface and can move the selected defects into other defect groups (e.g., class 3) on bottom, right hand side 84 of the user interface. Such moving of defects can be easily accomplished by clicking and dragging individual defect images. In a similar manner, the user may create one or more additional defect groups on the right hand side of the user interface. In addition, the user may assign individual defects to the additional defect group(s) as described above. The user interface may be further configured as shown in FIG. 6. In addition, the user interface may be further configured as described herein.

Any new defects detected by the computer-implemented method may be assigned to another defect group, which may be identified using a name such as "Probable New Defect Types" and may also be illustrated in the left hand side of the user interface along with all of the other defect groups. In this manner, when working from a recipe, if there are defects that do not match any previously classified defects, the user can be prompted to handle these defects separately. In addition, the defect groups that are illustrated in the user interface may also include a defect group for defects that were not detected during review. Such defects may be flagged as No Defect Found or "NDF" and can be shown in a group named, for example, "SEM Non-Visuals" in the case of SEM-based review. The user interface may prompt the user to handle these defects separately. The information about these defects that is displayed in the user interface may include low magnification images of the defects generated by optical inspection during which the defects were detected.

Figure 7:
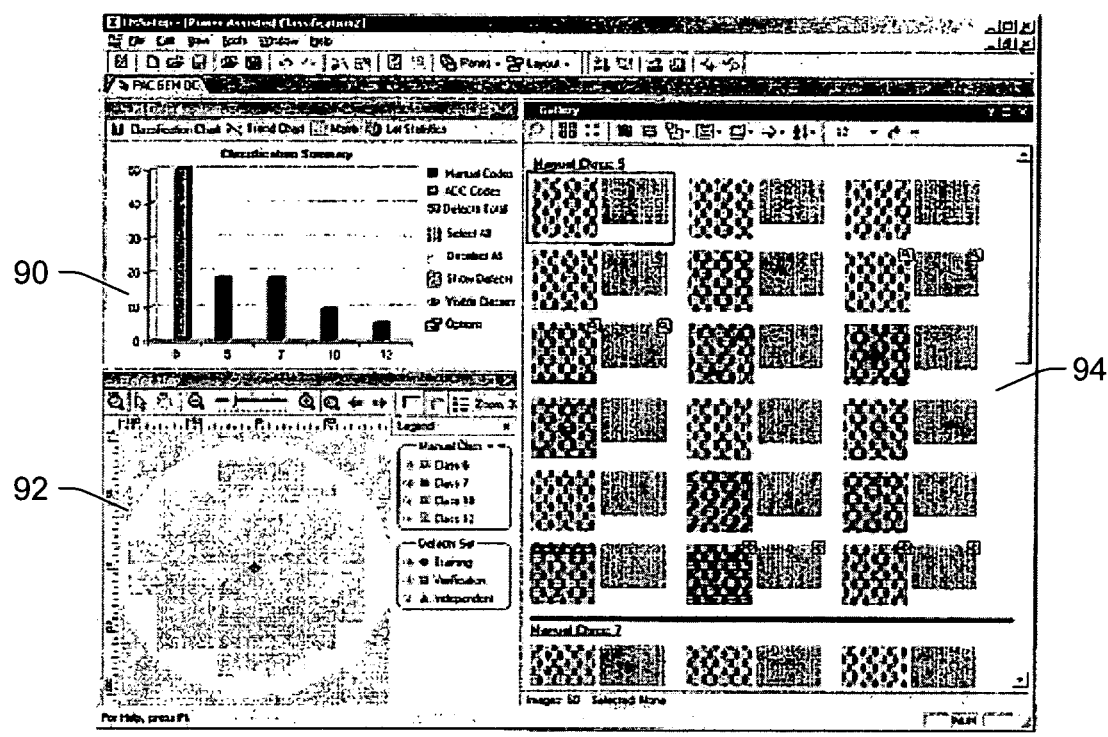

FIG. 7 is an additional screenshot that illustrates a different example of a user interface that can be used to perform one or more of the functions described above. This user interface illustrates the results that may be displayed to a user after the computer-implemented has been performed. For example, the user interface displays chart 90 illustrating the results of the classification. In addition, the user interface displays wafer map 92, which illustrates the different classes of defects and the locations of the defects on the wafer. The user interface also displays defect gallery 94, which illustrates the defects as arranged in the defect groups and any classifications that were assigned to the defect groups by the user. Although only the defects in manual class 5 and manual class 7 are illustrated in FIG. 7, it is to be understood that defects in other classes may be illustrated using, for example, the scroll bar to the right of the defect gallery.

The user interface may be further configured as shown in FIG. 7. In addition, the user interface may be configured to perform additional functions described herein or any other functions known in the art. For example, the user interface may be configured to allow the user to tag defects to indicate which defects the user would like to be shipped. In one such example, the classifications (and optionally images selected during the classification method) can be sent for further analysis using a KLARF or other standard file. In addition, the user interface may be configured to allow the user to send the results to a database such as a fab database.

Further modifications and alternative embodiments of various aspects of the invention may be apparent to those skilled in the art in view of this description. For example, computer-implemented methods for classifying defects on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for classifying defects on a specimen, comprising:
    automatically assigning individual defects detected on the specimen to defect groups based on one or more characteristics of the individual defects, wherein a user does not assign the individual defects to the defect groups one at a time in the assigning step;
    subsequent to said assigning, displaying information about the defect groups to the user, wherein the information comprises information about one or more typical defects included in each of the defect groups, wherein said displaying is not performed until after the one or more typical defects and other defects have been assigned to the defect groups; and
    allowing the user to assign a classification to each of the defect groups, wherein said assigning, said displaying, and said allowin are performed by a computer system.

2. The method of claim 1, wherein the one or more characteristics comprise defect feature vectors, extracted features, feature attributes, or some combination thereof.

3. The method of claim 1, wherein the one or more characteristics are determined from data generated by electron beam review of the individual defects.

4. The method of claim 1, wherein the one or more characteristics are determined from data generated by electron beam review of the individual defects in combination with data generated by optical inspection of the specimen.

5. The method of claim 1, further comprising selecting a classification recipe based on one or more characteristics of the specimen, wherein said assigning comprises using the classification recipe to assign the individual defects to the defect groups.

6. The method of claim 1, further comprising selecting a classification recipe based on one or more processes performed on the specimen, wherein said assigning comprises using the classification recipe to assign the individual defects to the defect groups.

7. The method of claim 1, wherein said assigning comprises using automatic defect classification codes to assign the individual defects to the defect groups.

8. The method of claim 1, wherein said assigning comprises using natural grouping to assign the individual defects to the defect groups.

9. The method of claim 1, wherein the defect groups comprise a defect group for the individual defects that have one or more unrecognized characteristics.

10. The method of claim 1, wherein the defect groups comprise a defect group for the individual defects that were detected by inspection but were not re-detected by review.

11. The method of claim 1, wherein the information further comprises probable classifications for the defect groups.

12. The method of claim. 1, wherein the information further comprises data about one or more of the individual defects, and wherein the data is generated by an electron beam review tool.

13. The method of claim 1, wherein the information further comprises data about one or more of the individual defects, and wherein the data is generated by an optical inspection tool.

14. The method of claim 1, further comprising allowing the user to move one or more of the individual defects from one of the defect groups to another of the defect groups.

15. The method of claim 1, further comprising allowing the user to create one or more additional defect groups and to move one or more of the individual defects from the defect groups into the one or more additional defect groups.

16. The method of claim 1, further comprising generating a classification recipe based on the classifications assigned by the user, wherein the classification recipe can be used in semi-automatic defect classification methods and automatic defect classification methods.

17. The method of claim 1, wherein said assigning comprises using a classification recipe to assign the individual defects to the defect groups, the method further comprising altering the classification recipe based on the classifications assigned by the user.

18. The method of claim 1, further comprising generating a training set based on the classifications assigned by the user.

19. The method of claim 1, further comprising analyzing the individual defects, the specimen, processes performed on the specimen, or a combination thereof based on the classifications assigned by the user.

20. The method of claim 1, further comprising making yield management decisions based on the classifications assigned by the user.

21. A computer-implemented method for classifying defects on a specimen, comprising:
    automatically assigning individual defects detected on the specimen to defect groups based on one or more characteristics of the individual defects, wherein a user does not assign the individual defects to the defect groups one at a time in the assigning step;
    subsequent to said assigning, displaying information about the defect groups to the user, wherein the information comprises a classification assigned to each of the defect groups and information about one or more typical defects included in each of the defect groups, wherein said displaying is not performed until after the one or more typical defects and other defects have been assigned to the defect groups; and
    allowing the user to confirm or alter the classification assigned to each of the detect groups, wherein said assigning, said displaying, arid said allowing are performed by a computer system.

22. A system configured to classify defects on a specimen, comprising:
    a non-transitory computer-readable medium storing program instructions executable on a processor for automatically assigning individual defects detected on the specimen to detect groups based on one or more characteristics of the individual defects, wherein a user does not assign the individual defects to the defect groups one at a time in the assigning step; and
    a user interface configured for subsequent to said assigning, displaying information about the defect groups to a user, wherein the information comprises information about one or more typical defects included in each of the defect groups, wherein said displaying is not performed until after the one or more typical defects and other defects have been assigned to the defect groups, and allowing the user to assign a classification to each of the defect groups.

23. The system of claim 22, wherein said allowing comprises allowing the user to confirm or reject a classification that is assigned to each of the defect groups by the program instructions.

24. The system of claim 22, wherein said allowing comprising allowing the user to alter a classification that is assigned to each of the defect groups by the program instructions.

* * * * *